United States Patent
Knoch et al.

(10) Patent No.: US 7,079,966 B2
(45) Date of Patent: Jul. 18, 2006

(54) METHOD OF QUALIFYING A PROCESS TOOL WITH WAFER DEFECT MAPS

(75) Inventors: John A. Knoch, Portland, OR (US); Deborah A. Leek, Washougal, WA (US); Nathan Strader, Portland, OR (US)

(73) Assignee: LSI Logic Corporation, Milpitas, CA (US)

( * ) Notice: Subject to any disclaimer, the term of this patent is extended or adjusted under 35 U.S.C. 154(b) by 318 days.

(21) Appl. No.: 10/658,168

(22) Filed: Sep. 8, 2003

(65) Prior Publication Data

US 2005/0065739 A1    Mar. 24, 2005

(51) Int. Cl.
*G01N 31/00*    (2006.01)
(52) U.S. Cl. ....................................................... 702/81
(58) Field of Classification Search .................. 702/81
See application file for complete search history.

(56) References Cited

U.S. PATENT DOCUMENTS 5,870,187 A * 2/1999 Uritsky et al. ........... 356/237.2
6,701,259 B1 * 3/2004 Dor et al. ..................... 702/35

* cited by examiner

*Primary Examiner*—John Barlow
*Assistant Examiner*—Cindy D. Khuu
(74) *Attorney, Agent, or Firm*—Eric James Whitesell (57) ABSTRACT

A method of qualifying a process tool includes steps of: (a) finding a plurality of pre-scan defect locations on a surface of a semiconductor wafer; (b) subjecting the semiconductor wafer to processing by the process tool; (c) finding a plurality of post-scan defect locations on the surface of the semiconductor wafer; and (d) calculating a plurality of defect locations added by the process tool from the pre-scan defect locations and the post-scan defect locations.

10 Claims, 10 Drawing Sheets

| Tool Slot #1 Cassette Sl# | Tool Slot #1 Pre Scan | Tool Slot #1 Post Scan | Tool Slot #1 Adders | Tool Slot #50 Cassette Sl# | Tool Slot #50 Pre Scan | Tool Slot #50 Post Scan | Tool Slot #50 Adders |
|---|---|---|---|---|---|---|---|
| Slot 1 | 80 | 135 | 55 | Slot 50 | 70 | 23 | -47 |
| Slot 1 | 72 | 390 | 288 | Slot 50 | 61 | 114 | 53 |
| Slot 1 | 75 | 260 | 195 | Slot 50 | 136 | 203 | 67 |
| Slot 1 | 90 | 298 | 208 | Slot 50 | 76 | 106 | 30 |
| Slot 1 | 134 | 206 | 72 | Slot 50 | 148 | 179 | 31 |
| Slot 1 | 84 | 223 | 139 | Slot 50 | 143 | 166 | 23 |
| Slot 1 | 83 | 195 | 112 | Slot 50 | 148 | 162 | 14 |
| Slot 1 | 113 | 1087 | 974 | Slot 50 | 101 | 1002 | 900 |
| Slot 1 | 124 | 428 | 304 | Slot 50 | 124 | 274 | 150 |
| Slot 1 | 152 | 1215 | 1063 | Slot 50 | 116 | 209 | 93 |

FIG._9C

METHOD OF QUALIFYING A PROCESS TOOL WITH WAFER DEFECT MAPS

BACKGROUND OF THE INVENTION

1. Field of the Invention

The present invention relates generally to the manufacture of integrated circuits. More specifically, but without limitation thereto, the present invention relates to methods of evaluating equipment defects for qualifying process tools used in the manufacture of integrated circuit dies on semiconductor wafers.

2. Description of Related Art

In previous methods used for qualifying process tools used in the manufacture of integrated circuit dies, equipment defects are evaluated by counting the number of defective dies on a wafer, transferring the wafer to a process tool, processing the wafer in the process tool, returning the wafer from the process tool, counting the number of defects on the wafer again, and subtracting the first defect count from the second to obtain the number of defects that were added to the wafer by the process tool. If more than a predetermined number of defects, or "adders", were added to a wafer during the qualification check, then the process tool fails the qualification check. An investigation into the cause of the performance is then conducted to find a repair solution. When the process tool has been repaired, the qualification test is repeated, and so on, until the process tool passes the qualification test. At that point, production runs may be made with minimum loss in yield due to the process tool performance. Disadvantageously, identifying the cause of a problem in the process tool performance may require a large amount of time, which translates into higher production costs.

SUMMARY OF THE INVENTION

In one aspect of the present invention, a method of qualifying a process tool includes steps of: (a) finding a plurality of pre-scan defect locations on a surface of a semiconductor wafer; (b) subjecting the semiconductor wafer to processing by the process tool; (c) finding a plurality of post-scan defect locations on the surface of the semiconductor wafer; and (d) calculating a plurality of defect locations added by the process tool from the pre-scan defect locations and the post-scan defect locations.

In another aspect of the present invention, a computer program product for qualifying a process tool includes:
  a medium for embodying a computer program for input to a computer; and
  a computer program embodied in the medium for causing the computer to perform steps of:
    (a) finding a plurality of pre-scan defect locations on a surface of a semiconductor wafer;
    (b) subjecting the semiconductor wafer to processing by the process tool;
    (c) finding a plurality of post-scan defect locations on the surface of the semiconductor wafer; and
    (d) calculating a plurality of defect locations added by the process tool from the pre-scan defect locations and the post-scan defect locations.

BRIEF DESCRIPTION OF THE DRAWINGS

The present invention is illustrated by way of example and not limitation in the accompanying figures, in which like references indicate similar elements throughout the several views of the drawings, and in which.

Elements in the figures are illustrated for simplicity and clarity and have not necessarily been drawn to scale. For example, the dimensions of some elements in the figures may be exaggerated relative to other elements to point out distinctive features in the illustrated embodiments of the present invention.

DESCRIPTION OF THE ILLUSTRATED EMBODIMENTS

Figure 1:
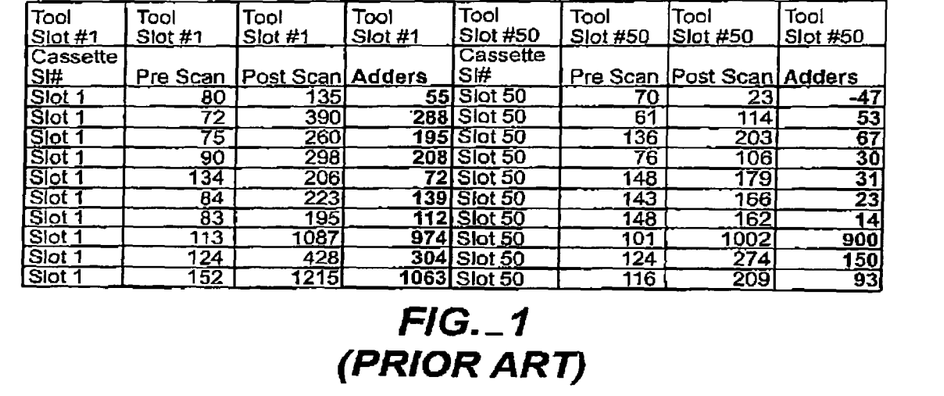
FIG. 1 illustrates a typical spreadsheet of the prior art for displaying the results of a process tool qualification check.

FIG. 1 illustrates a typical spreadsheet of the prior art for displaying the results of a process tool qualification check.

To generate the results shown in the example of FIG. 1, two wafers are scanned by a laser beam. The wafers may be patterned with integrated circuit dies, or the wafers may be unpatterned. In either case, any particles or scratches on the surface of each wafer will deflect the scanning laser beam to a photodetector. The photodetector generates a pulse each time the laser beam is deflected that increments a total defect count for each wafer. The total defect count for each wafer is recorded in a "pre-scan" column corresponding to each wafer.

The two wafers are then inserted, for example, into slots #1 and #50 respectively of the process tool and are processed by the process tool. After processing, the wafers are returned from the process tool and are again scanned by the laser beam. The total defect count for each wafer is then recorded in the "post-scan" column corresponding to each wafer. The difference between the defect count in each pre-scan columns and the defect count in the corresponding post-scan column is calculated in the spreadsheet and inserted in the "adders" column for the corresponding wafer. The qualification test is then repeated several times, each time with a new pair of wafers. If the adder count exceeds a selected threshold in any of the repeated tests, the process tool fails the qualification check and is shut down to investigate the cause of the problem.

A disadvantage of the method of qualifying process tools illustrated by the spreadsheet of FIG. 1 is that only the number of defects added by the process tool is displayed, while valuable spatial information about the locations of the defects is lost. Also, it is possible for a tool to remove existing defects and to add new defects. To avoid this problem, clean test wafers are required. More testing is generally required to identify the locations of the defects, resulting in extended containment times and multiple equipment failures before a problem may be found and corrected.

In one aspect of the present invention, the progress of a process tool qualification test is advantageously displayed in a graphic plot that displays the added defects versus a failure threshold and wafer maps that display the spatial signature of pre-scan, post-scan, and added defects for each wafer tested. In one embodiment, a method of qualifying a process tool includes steps of: (a) finding a plurality of pre-scan defect locations on a surface of a semiconductor wafer; (b) subjecting the semiconductor wafer to processing by the process tool; (c) finding a plurality of post-scan defect locations on the surface of the semiconductor wafer; and (d) calculating a plurality of defect locations added by the process tool from the pre-scan defect locations and the post-scan defect locations.

Figure 2:
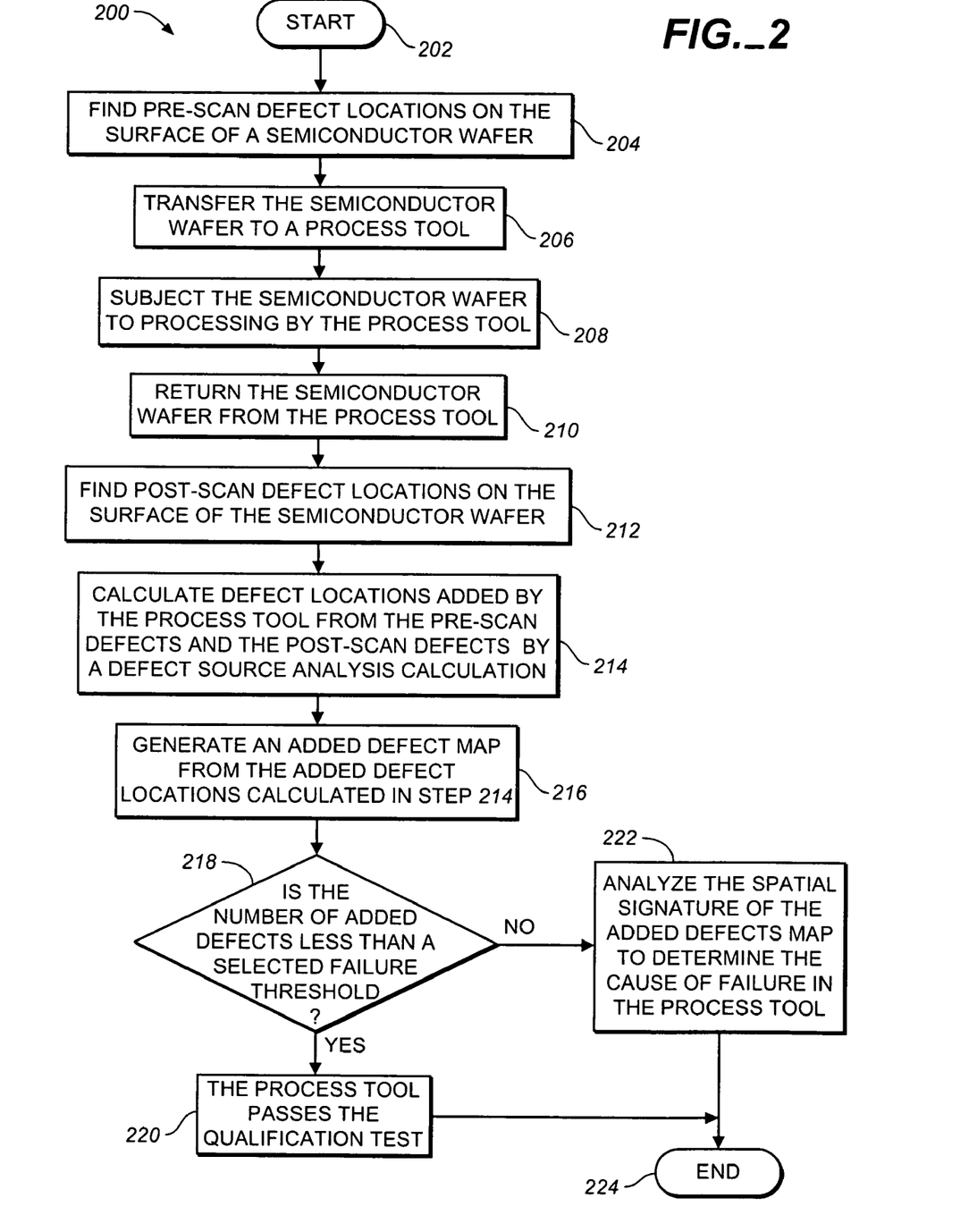
FIG. 2 illustrates a flow chart for a method of qualifying a process tool according to an embodiment of the present invention.

FIG. 2 illustrates a flow chart 200 for a method of qualifying a process tool according to an embodiment of the present invention.

Step 202 is the entry point of the flow chart 200.

In step 204, pre-scan defect locations are found on the surface of a semiconductor wafer according to well-known techniques, for example, by a scanning laser beam or an optical microscope. The semiconductor wafer may be patterned with integrated circuit dies, or the semiconductor wafer may be unpatterned.

In step 206, the semiconductor wafer is transferred to a process tool, typically on a wafer cassette.

In step 208, the semiconductor wafer is subjected to processing by the process tool, for example, to form a layer of doped silicon on the semiconductor wafer.

In step 210, the semiconductor wafer is returned from the process tool, typically on a wafer cassette.

In step 212, post-scan defect locations on surface of the semiconductor wafer are found, for example, by the same method used to find the pre-scan defect locations in step 204. Alternatively, different methods and different equipment may be used according to well-known techniques to find the post-scan defect locations on surface of semiconductor wafer, especially if the test is performed on an actual product.

In step 214, the defect locations added by the process tool are calculated from the pre-scan defect locations and the post-scan defect locations by a defect source analysis calculation.

In step 216, an added defect map is generated from the added defect locations calculated in step 214.

In step 218, if the number of added defects is less than a selected failure threshold, then control is transferred to step 220. If the number of added defects exceeds the selected failure threshold, then control is transferred to step 222.

In step 220, the process tool passes the qualification test, and control is transferred to step 224.

In step 222, the spatial signature of the added defects on the added defect map is analyzed to determine the cause of failure in the process tool.

Step 224 is the exit point of the flow chart 200.

Figure 3:
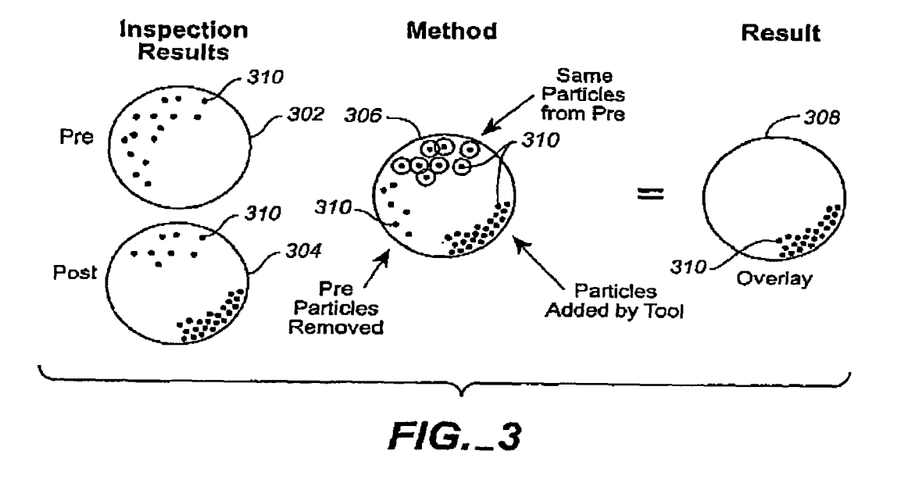
FIG. 3 illustrates a diagram of a defect source analysis calculation according to an embodiment of the present invention.

FIG. 3 illustrates a diagram of a defect source analysis calculation according to an embodiment of the present invention. Shown in FIG. 3 are a pre-test wafer map 302, a post-test wafer map 304, a summed overlay map 306, an added defect map 308, and defect locations 310.

In FIG. 3, the pre-test wafer map 302 shows the defect locations 310 resulting from scratches and particles on the surface of the wafer that were detected by a laser scan as described above. The post-test wafer map 304 shows the defect locations 310 after the wafer was returned from the process tool. It is possible that some of the particles on the surface of the wafer that appear as defect locations 310 on the pre-test wafer map 302 become dislodged in the process tool and do not appear on the post-test wafer map 304. A disadvantage of previous methods for calculating the number of defects added by the process tool is the failure to account for the removal of particles from the pre-test wafer map 302. The method of the present invention overcomes this disadvantage by using the locations of the defects to determine which defects were added by the process tool.

The circled defect locations 310 in the summed overlay map 306 are in identical or nearly identical locations on both the pre-test wafer map 302 and the post-test wafer map 304. The uncircled defect locations 310 in the lower left portion of the summed overlay map 306 represent the particles that were removed by the process tool and do not appear on the post-test wafer map 304. The remaining defect locations 310 in the lower right portion of the summed overlay map 306 represent defects that were added by the process tool and do not appear in the pre-test wafer map 302. The defect source analysis calculation of the present invention advantageously distinguishes defect locations 310 that are added by the process tool (adders) from defects that were not added by the process tool (non-adders) to generate the added defect map 308.

FIGS. 4A–4D illustrate a flow chart 400 of an example of a defect source analysis calculation that may be used to generate the added defect map 308 of FIG. 3. Other methods of generating the added defect map 308 in FIG. 3 may be used to practice various embodiments of the present invention within the scope of the appended claims.

Figure 4A:
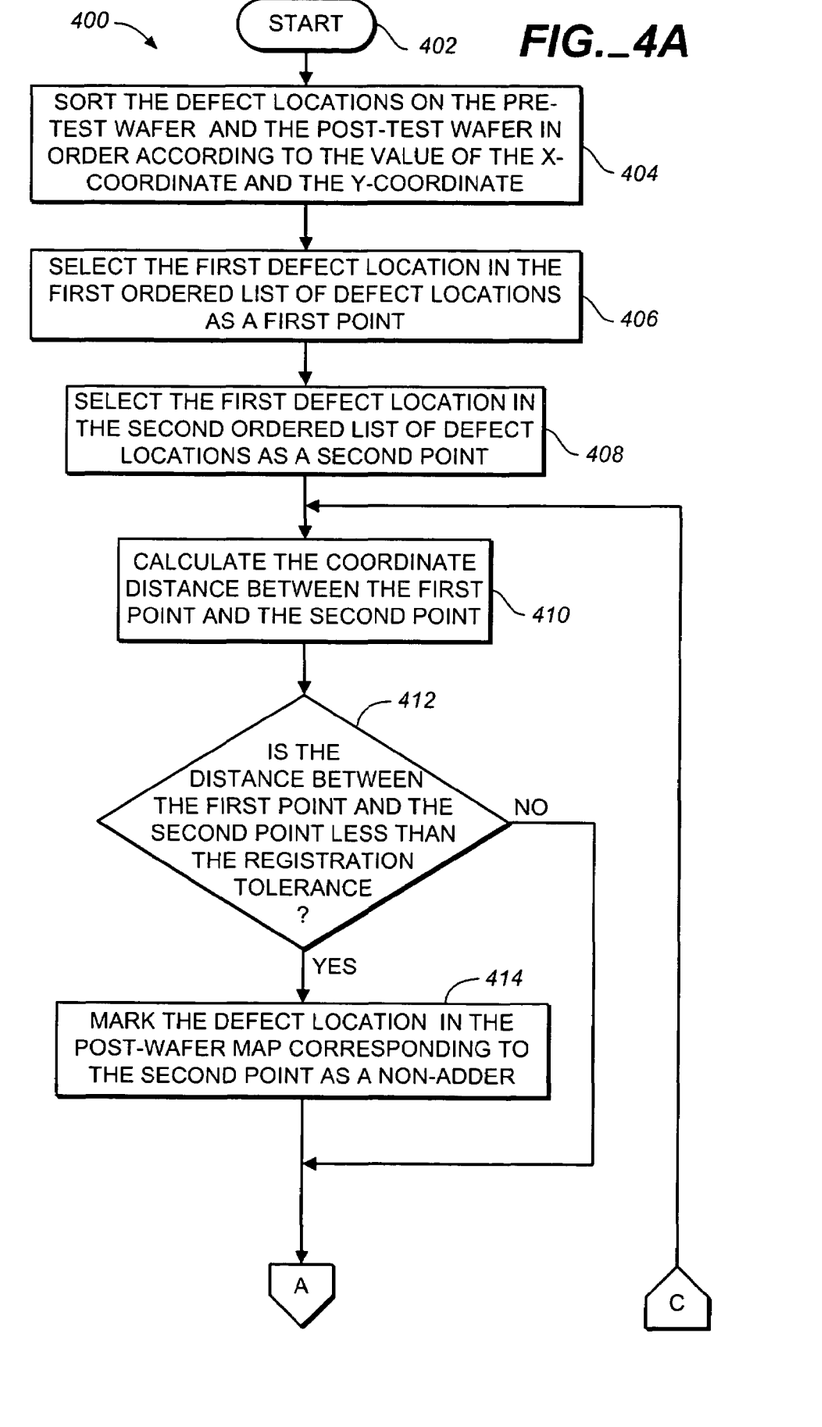
FIGS. 4A–4D illustrate a flow chart of an example of a defect source analysis calculation that may be used to generate the added defect map of FIG. 3.

Step 402 is the entry point of the flow chart 400.

In step 404, the defect locations 310 on the pre-test wafer 302 and the post-test wafer 304 are sorted in order according to the value of the X-coordinate of each defect location 310. Defect locations 310 having the same X-coordinate are further sorted according to the value of the Y-coordinate. For example, the defect locations (2,6), (1,3), (4,5), (3,2), (5,1), and (3,1) would be sorted in the following order: (1,3), (2,6), (3,1), (3,2), (4,5), and (5,1). The sorted defect locations are stored in a first list of ordered defect locations from the pre-test wafer map 302 and in a second list of ordered defect locations from the post-test wafer map 304. Alternatively, the first list of ordered defect locations may be sorted from the pre-test wafer map 302 and the second list of ordered defect locations may be sorted from the post-test wafer map 304.

In step 406, the first defect location in the first ordered list of defect locations is selected as a first point.

In step 408, the first defect location in the second ordered list of defect locations is selected as a second point.

Figure 5A:
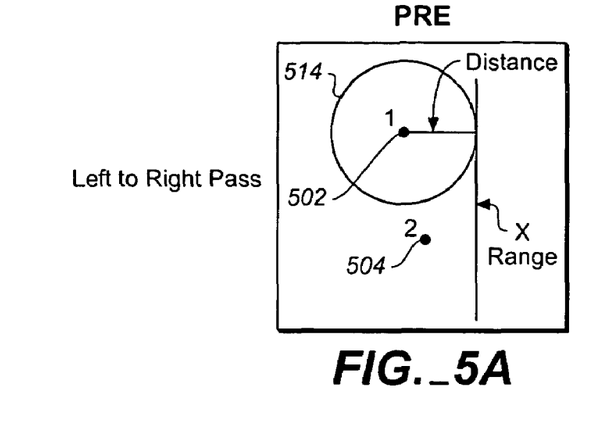
FIGS. 5A and 5B illustrate a first part of a calculation to determine whether a defect location in the pre-test wafer map is an added defect on the post-test wafer map of FIG. 3.
Figure 5B:
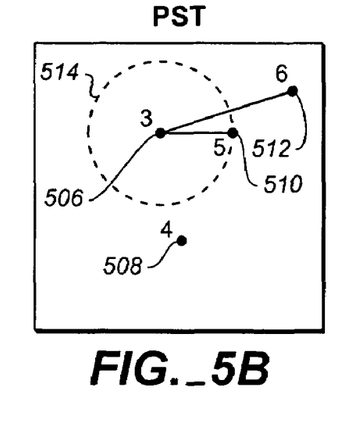

FIGS. 5A and 5B illustrate a first part of a calculation to determine whether a defect location in the pre-test wafer map 302 is an added defect on the post-test wafer map 304 of FIG. 3. Shown in FIGS. 5A and 5B are defect locations 502 and 504 on the pre-test wafer map, defect locations 506, 508, 510 and 512 on the post-test wafer map, and a registration tolerance 514.

In FIG. 5A, the defect location 502 in the pre-test wafer map is selected as the first point. The defect location 506 in the post-test wafer map is selected as the second point.

In step 410, the coordinate distance between the first point $(x_1, y_1)$ and the second point $(x_2, y_2)$ is calculated, for example, from a lookup table or from the distance formula $[(x_1-x_2)^2+(y_1-y_2)^2]^{1/2}$.

In step 412, if the distance between the first point and the second point is less than the registration tolerance, then control is transferred to step 414. Otherwise, control is transferred to step 416. The registration tolerance typically has a radius equal to a value of about 20 microns to 50 microns, if the wafer maps are aligned. If the wafer maps are subject to offset errors from scanning or inspection tool offset, then a higher registration tolerance may be used, for example, 1000 microns or more.

In step 414, the defect location 310 in the post-wafer map 304 corresponding to the second point is marked as a non-adder, because it is considered to be identical to the first point on the pre-test wafer map 302.

In the example of FIGS. 5A and 5B, the registration tolerance 514 is compared to the coordinate distance calculated in step 412 between the defect location 502 and the defect location 506. Because the coordinate distance between the defect location 502 and the defect location 506 falls inside the registration tolerance 514, the defect locations 502 and 506 are considered to be the same defect on both the pre-test wafer amp and the post-test wafer map, therefore this defect is marked as a non-adder defect on the post-test wafer map.

Figure 4B:
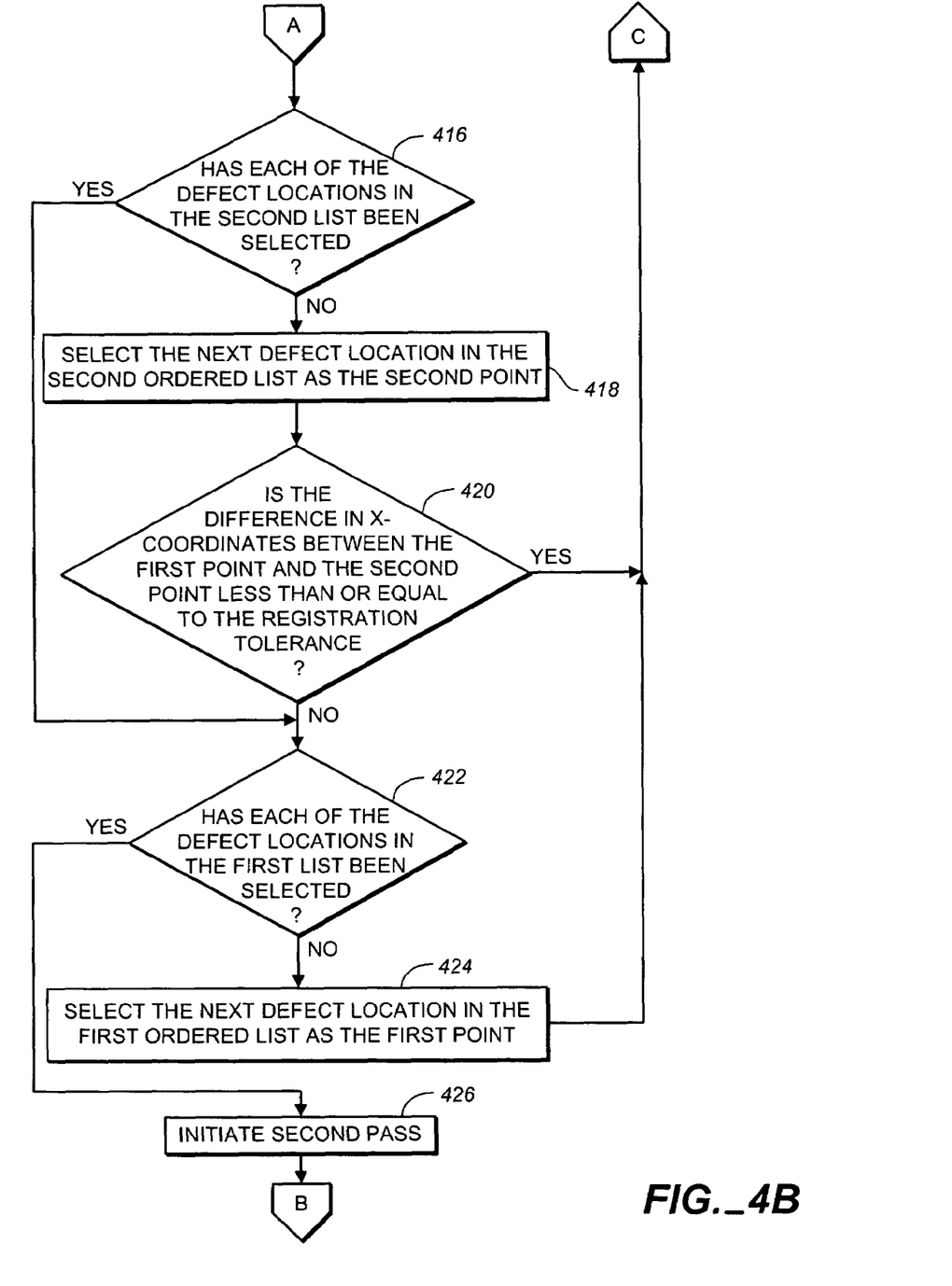

In step 416, if each of the defect locations in the second list has been selected, then control is transferred to step 422. Otherwise, control is transferred to step 418.

In step 418, the next defect location in the second ordered list is selected as the second point. In the example of FIGS. 5A and 5B, the new second point is the defect location 508 in the post-test wafer map. The first point is still the defect location 502 in the pre-test wafer map.

In step 420, if the difference in X-coordinates between the first point and the second point is less than or equal to the registration tolerance, then there may still be one or more defects on the post-test wafer map that may be marked as non-adders, so control is transferred back to step 410. If the difference in X-coordinates between the first point and the second point is greater than the registration tolerance, then no subsequent defect locations in the second ordered list may be marked as non-adders, so control is transferred to step 422. In the example of FIGS. 5A and 5B, the difference in X-coordinates between defect locations 502 and 508 is less than the registration tolerance, so control is transferred back to step 410.

In step 422, if each of the defect locations in the first ordered list has been selected, then control is transferred to step 426. Otherwise, control is transferred to step 424.

In step 424, the next defect location 504 in the first ordered list is selected as the first point, and control is transferred back to step 410.

In step 426, the pass from left to right through the ordered lists of the defect locations has been completed. In some cases, such as the example of, FIGS. 5A and 5B, there may be defect locations on the post-test wafer map that were omitted from a comparison on the left-to-right pass that would have marked a defect location on the post-test map as a non-adder. An example of such a possible omission is the defect location 508. A second pass may be made from right to left through the first ordered list of defect locations and the second ordered list of defect locations, that is, in reverse order, to capture the omitted non-adders as follows. After completing the left-to-right pass, the last defect location in the first list of defect locations is the new first point, and the last defect location in the second list of defect locations is the new second point.

Figure 6A:
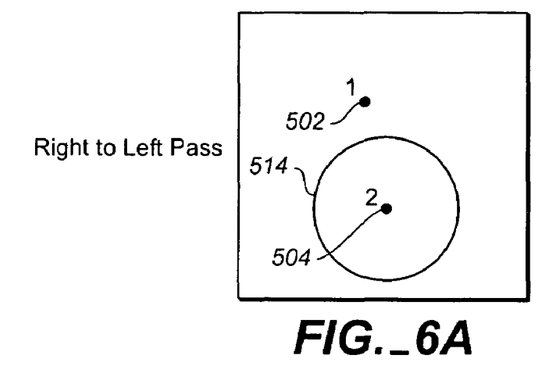
FIGS. 6A and 6B illustrate the second part of a calculation to determine whether a defect location in the pre-test wafer map is an added defect on the post-test wafer map of FIG. 3.
Figure 6B:
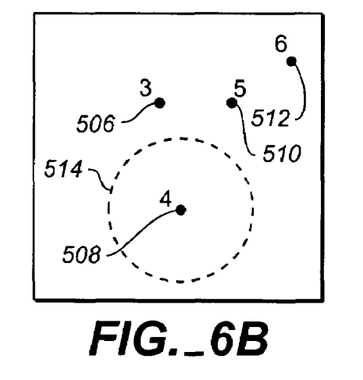

FIGS. 6A and 6B illustrate the second part of a calculation to determine whether a defect location in the pre-test wafer map 302 is an added defect on the post-test wafer map 304 of FIG. 3. Shown in FIGS. 6A and 6B are defect locations 502 and 504 on the pre-test wafer map, defect locations 506, 508, 510 and 512 on the post-test wafer map, and a registration tolerance 514.

In FIG. 6A, the defect location 504 on the pre-test wafer map is now the selected first point, and the defect location 512 is now the selected second point.

Figure 4C:
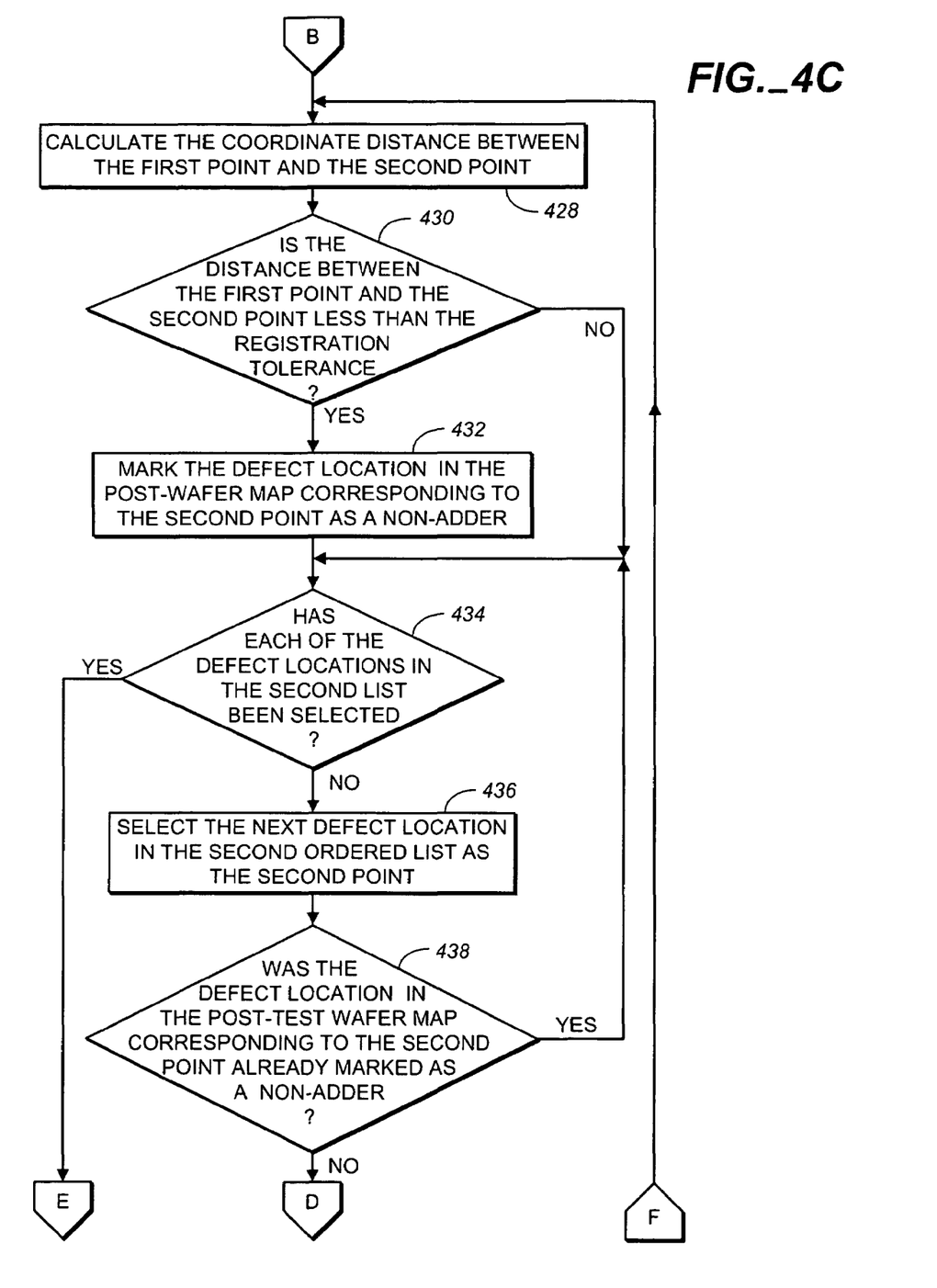

In step 428, the coordinate distance between the first point and the second point is calculated as described above.

In step 430, if the distance between the first point and the second point is less than the selected registration tolerance, then control is transferred to step 432. Otherwise, control is transferred to step 434.

In the example of FIGS. 6A and 6B, the registration tolerance 514 is compared to the coordinate distance calculated in step 428 between the defect location 504 on the pre-test wafer map and the defect location 512 on the post-test wafer map. Because the coordinate distance between the defect location 504 and the defect location 512 falls outside the registration tolerance 514, the defect location 512 is an added defect on the post-test wafer map. Either the added defects, the non-added defects, or both may be marked on the list of post-test defect locations to calculate the added defect locations.

In step 432, the corresponding defect location in the post-wafer map is marked as a non-added defect.

In step 434, if each of the defect locations in the second ordered list have been selected on the second pass, then control is transferred to step 442. Otherwise, control is transferred to step 436.

In step 436, the next right-most defect location in the second ordered list is selected as the new second point. In the example of FIGS. 6A and 6B, the next defect location in the second ordered list is the defect location 510.

Figure 4D:
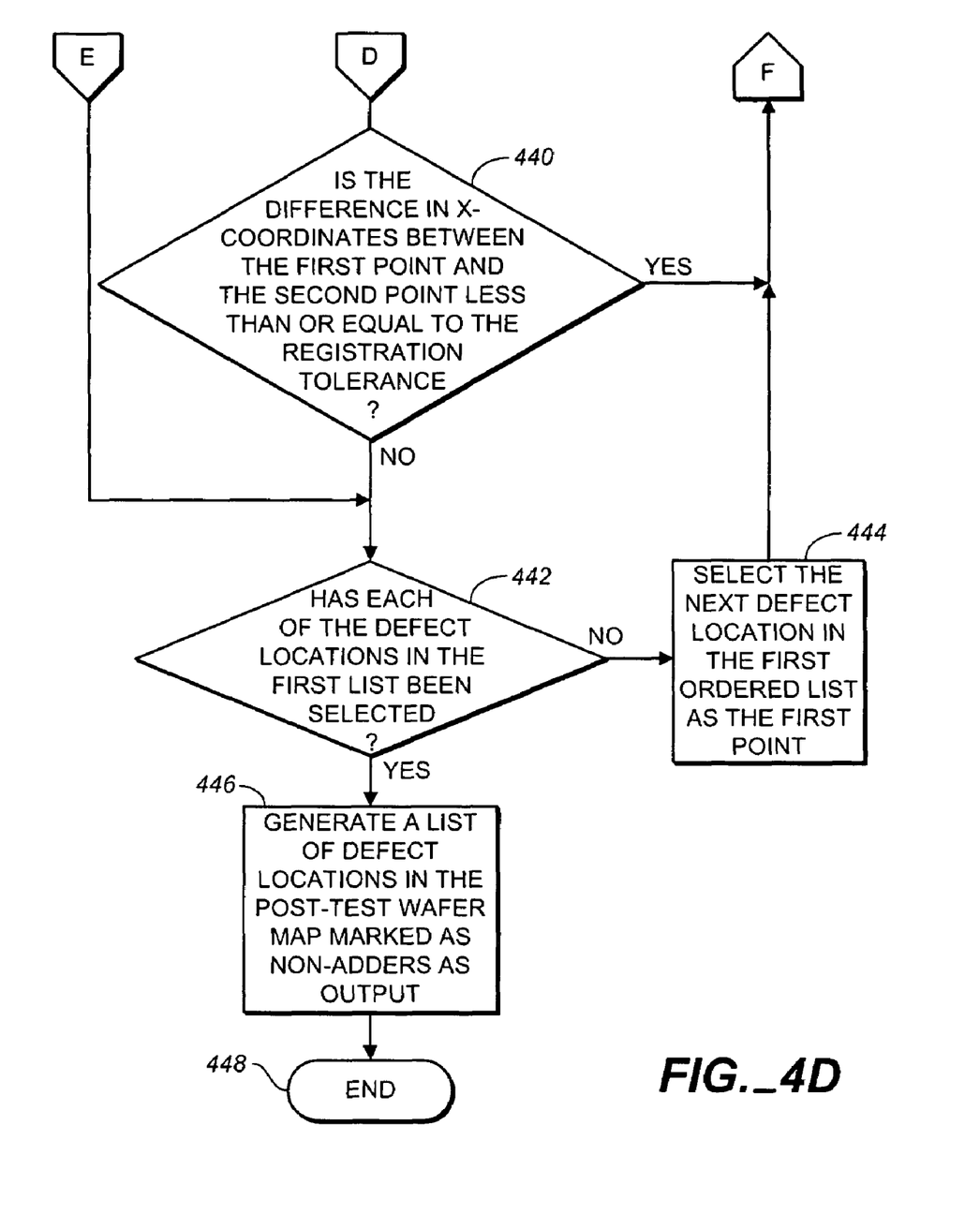

In step 438, if the defect location in the post-test wafer map corresponding to the second point was already marked as a non-adder, then control is passed to step 434. Otherwise, control is passed to step 440. In the example of FIGS. 6A and 6B, the defect location 510 was already marked as a non-adder, so control is passed to step 434.

In step 440, if the difference in X-coordinates between the first point and the second point is less than the registration tolerance, then there may be additional defects on the post-test wafer map that may be marked as non-adders, so control is transferred to step 428. Otherwise, control is transferred to step 442. In the example of FIGS. 6A and 6B, the difference in X-coordinates between defect locations 504 and 512 is less than the registration tolerance, so control is transferred to step 428.

In step 442, if each of the defect locations in the first sorted list have already been selected, then control is transferred to step 446. Otherwise, control is transferred to step 444.

In step 444, the next defect location in the first ordered list is selected as the first point, and control is transferred to step 428.

In step 446, the pass from right to left through the lists of ordered coordinates has been completed, and a list of added defect locations in the post-test wafer map is generated as output from the marked defect locations.

Step 448 is the exit point of the flow chart 400.

Figure 7:
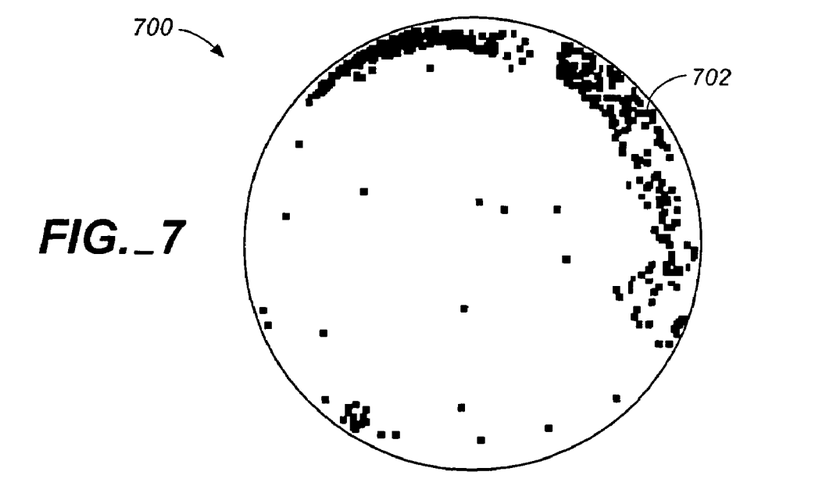
FIG. 7 illustrates an added defect map generated from the flow chart of FIG. 2.

FIG. 7 illustrates an added defect map 700 generated from the flow chart 200 of FIG. 2. Shown in FIG. 7 are added defect locations 702.

In FIG. 7, the added defects locations 702 are the defect locations on the post-test wafer map that remain after discarding the defect locations marked as non-adders by the defect source analysis calculation. The added defect locations 702 are illustrated in this example as darkened grid locations, however, other plotting symbols and colors may also be used to practice various embodiments of the present invention within the scope of the appended claims.

The added defect map 700 generated as described above may advantageously be used in conjunction with the pre-test wafer map, the post-test wafer map, and a scatter plot to qualify a process tool as follows.

Figure 8:
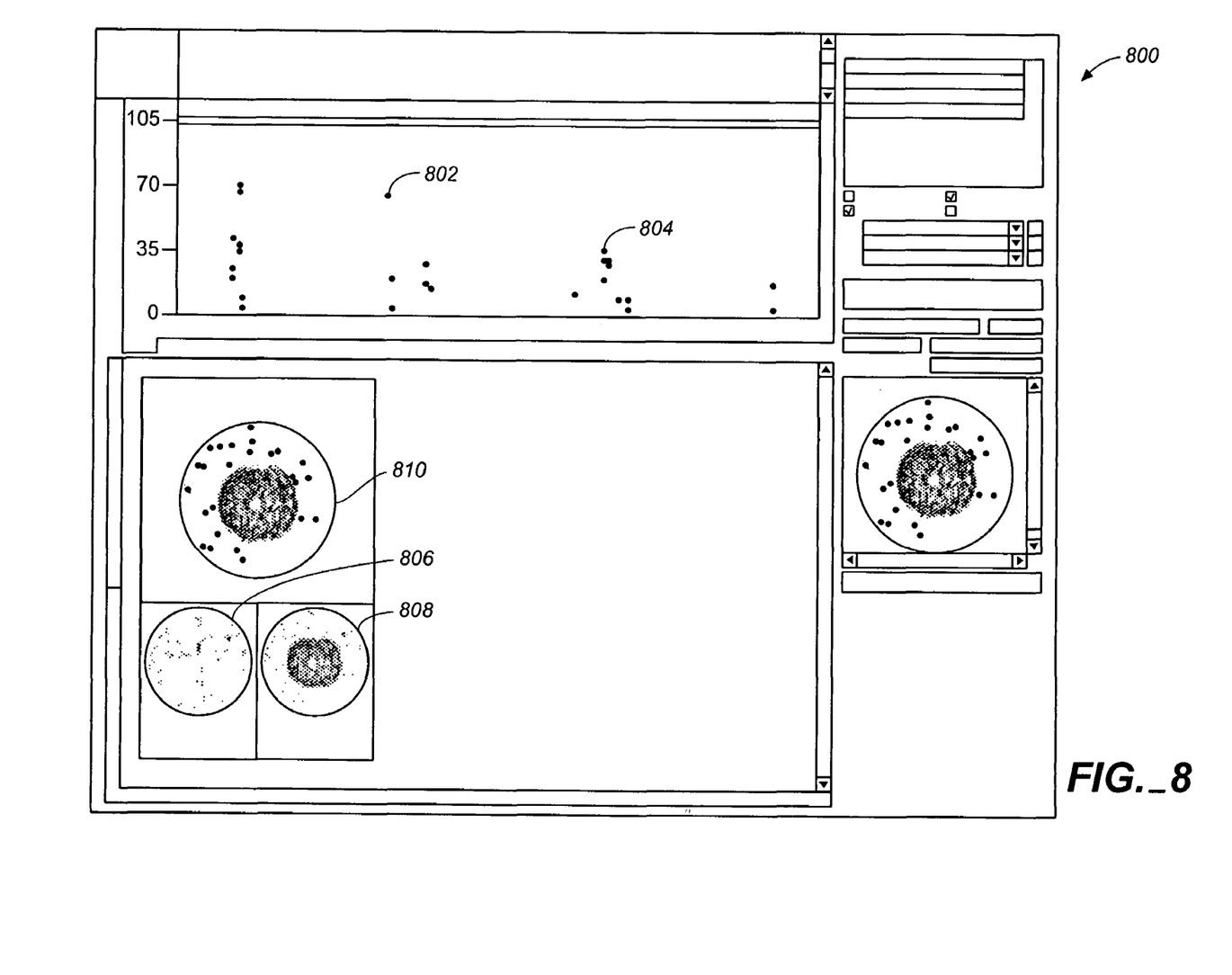
FIG. 8 illustrates a process tool qualification display according to an embodiment of the present invention.

FIG. 8 illustrates a process tool qualification display 800 according to an embodiment of the present invention. Shown in FIG. 8 are a scatter plot 802, points 804, a pre-test wafer map 806, a post-test wafer map 808, and an added defect map 810.

The scatter plot 802 displays each point 804 that is representative of the total number of added defects calculated for each corresponding wafer subjected to processing by the process tool. If the point falls above a selected failure threshold, the process tool is shut down to find and correct the problem. The operator may select any point 804 to initiate a display of the pre-test wafer map 806, the post-test wafer map 808, and the added defect map 810.

Figure 9A:
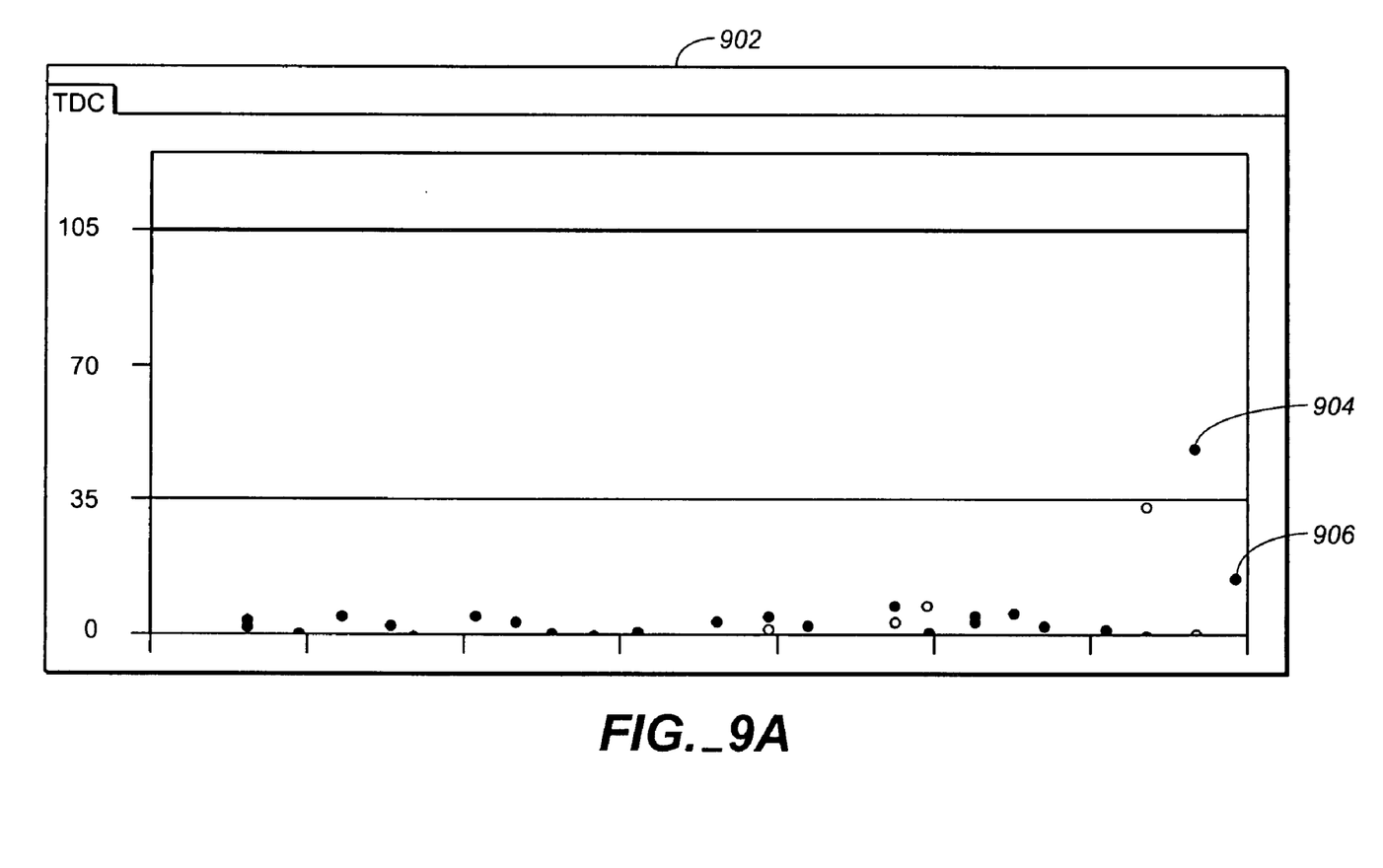
FIGS. 9A, 9B and 9C illustrate an example of how the process tool qualification display of FIG. 8 may be used to analyze a process tool failure.
Figure 9B:
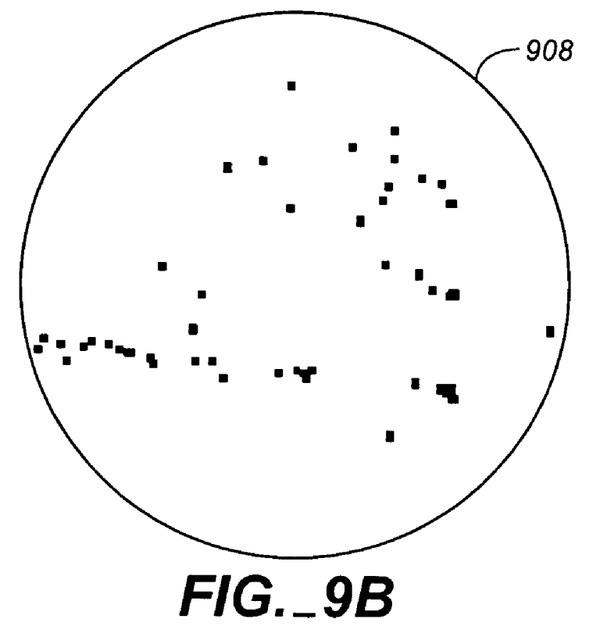
Figure 9C:
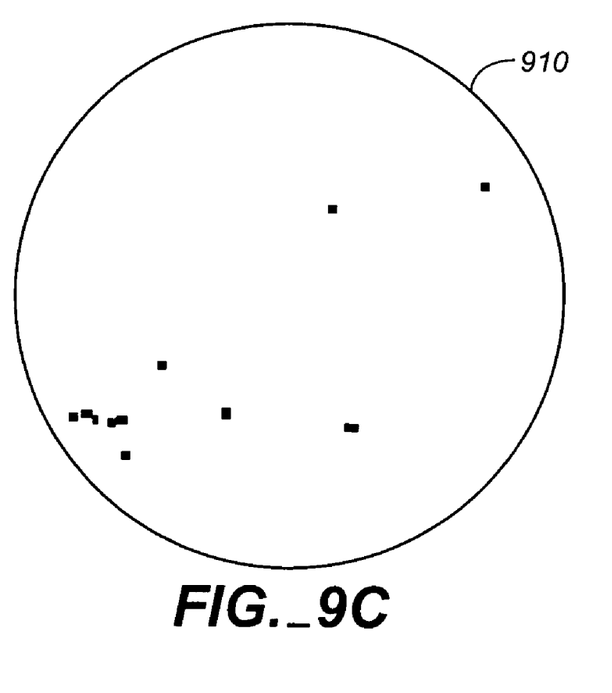

FIGS. 9A, 9B and 9C illustrate an example of how the process tool qualification display 800 of FIG. 8 may be used to analyze a process tool failure. Shown in FIGS. 9A, 9B and 9C are a scatter plot 902, points 904 and 906, and added defect maps 908 and 910.

In FIGS. 9A, 9B and 9C, a process tool failure is indicated by the point 904, which exceeds the selected failure threshold of 35 in this example. Clicking on or selecting the point 904 initiates the display of the added defect map 908. The spatial signature of the added defects forming a horizontal line in the lower part of the added defect map 908 indicates a scratch that was caused by the process tool. The process tool is shut down and the cause of the scratch is found and repaired. When the process tool is re-tested, the added defect count 906 is still somewhat higher than the normal range of the previous added defect counts. Clicking on the point 906 initiates the display of the added defect map 910. The spatial signature of the added defects in the same area in which the scratch was found before indicates that the malfunction in the process tool has not yet been fully corrected, even though the number of added defects is below the selected failure threshold. The wafer yield may therefore be further increased by re-examining the process tool to correct the malfunction that causes the scratch.

Although the method of the present invention illustrated by the flowchart descriptions above are described and shown with reference to specific steps performed in a specific order, these steps may be combined, sub-divided, or reordered without departing from the scope of the claims. Unless specifically indicated herein, the order and grouping of steps is not a limitation of the present invention.

The steps described above with regard to the flow chart 200 may also be implemented by instructions performed on a computer according to well-known programming techniques.

In another aspect of the present invention, a computer program product for qualifying a process tool includes:

a medium for embodying a computer program for input to a computer; and a computer program embodied in the medium for causing the computer to perform steps of:

(a) finding a plurality of pre-scan defect locations on a surface of a semiconductor wafer;

(b) subjecting the semiconductor wafer to processing by the process tool;

(c) finding a plurality of post-scan defect locations on the surface of the semiconductor wafer; and (d) calculating a plurality of defect locations added by the process tool from the pre-scan defect locations and the post-scan defect locations.

While the invention herein disclosed has been described by means of specific embodiments and applications thereof, numerous modifications and variations could be made thereto by those skilled in the art without departing from the scope of the invention set forth in the following claims.

What is claimed is:

1. A method of qualifying a process tool comprising steps of:

(a) finding a plurality of pre-scan defect locations on a surface of a semiconductor wafer;

(b) subjecting the semiconductor wafer to processing by a process tool after step (a);

(c) finding a plurality of post-scan defect locations on the surface of the semiconductor wafer after step (b);

(d) calculating which defects were added by the process tool from the pre-scan defect locations and the post-scan defect locations;

(e) displaying a scatter plot of a point representative of a total number of defects added by the process tool to the semiconductor wafer; and (f) selecting the point on the scatter plot to initiate a display of one of a pre-test wafer map, a post-test wafer map, and an added defect map of defects added by the process tool to the semiconductor wafer.

2. The method of claim 1 further comprising a step of associating a spatial signature of added defects from the added defect map with a process tool malfunction.

3. A method of qualifying a process tool comprising steps of:

(a) finding a plurality of pre-scan defect locations on a surface of a semiconductor wafer;

(b) subjecting the semiconductor wafer to processing by a process tool after step (a);

(c) finding a plurality of post-scan defect locations on the surface of the semiconductor wafer after step (b);

(d) calculating which defects were added by the process tool from the pre-scan defect locations and the post-scan defect locations by comparing a distance between a first point corresponding to a defect location in a first list of pre-test defect locations and a second point corresponding to a defect location in a second list of post-test defect locations with a registration tolerance; and (e) marking the defect location in the second list as a non-adder when the distance is less than the registration tolerance.

4. The method of claim 3 wherein the first list and the second list are sorted by X-coordinate.

5. The method of claim 4 wherein defect locations in the first list and the second list having identical X-coordinates are further sorted by Y-coordinate.

6. A computer program product for qualifying a process tool comprising:
   a medium for embodying a computer program for input to a computer; and
   a computer program embodied in the medium for causing the computer to perform steps of:
   (a) finding a plurality of pre-scan defect locations on a surface of a semiconductor wafer;
   (b) subjecting the semiconductor wafer to processing by a process tool after step (a);
   (c) finding a plurality of post-scan defect locations on the surface of the semiconductor wafer after step (b);
   (d) calculating which defects were added by the process tool from the pre-scan defect locations and the post-scan defect locations;
   (e) displaying a scatter plot of a point representative of a total number of defects added by the process tool to the semiconductor wafer; and
   (f) selecting the point on the scatter plot to initiate a display of one of a pre-test wafer map, a post-test wafer map, and an added defect map of defects added by the process tool to the semiconductor wafer.

7. The computer program product of claim 6 further comprising a step of associating a spatial signature of added defects from the added defect map with a process tool malfunction.

8. A computer program product for qualifying a process tool comprising:
   a medium for embodying a computer program for input to a computer; and
   a computer program embodied in the medium for causing the computer to perform steps of:
   (a) finding a plurality of pre-scan defect locations on a surface of a semiconductor wafer;
   (b) subjecting the semiconductor wafer to processing by a process tool after step (a);
   (c) finding a plurality of post-scan defect locations on the surface of the semiconductor wafer after step (b);
   (d) calculating which defects were added by the process tool from the pre-scan defect locations and the post-scan defect locations by comparing a distance between a first point corresponding to a defect location in a first list of pre-test defect locations and a second point corresponding to a defect location in a second list of post-test defect locations with a registration tolerance; and
   (e) marking the defect location in the second list as a non-adder when the distance is less than the registration tolerance.

9. The computer program product of claim 8 wherein the first list and the second list are sorted by X-coordinate.

10. The computer program product of claim 4 wherein defect locations in the first list and the second list having identical X-coordinates are further sorted by Y-coordinate.

* * * * *